United States Patent [19]

Grossner

[11] 4,122,851
[45] Oct. 31, 1978

[54] CARRIER AND SKIN-PROTECTING COVER FOR URINE BAGS

[76] Inventor: Dolores E. Grossner, 427 E. Jackson, Virden, Ill. 62690

[21] Appl. No.: 829,332

[22] Filed: Aug. 31, 1977

Related U.S. Application Data

[63] Continuation of Ser. No. 685,983, May 13, 1976, abandoned.

[51] Int. Cl.² .............................................. A61F 5/44
[52] U.S. Cl. ................................... 128/295; 128/272; 128/DIG. 15; 128/DIG. 24
[58] Field of Search ............... 128/294, 295, 283, 275, 128/272, DIG. 24, DIG. 15; 4/110; 150/1, 52 G; 224/5 H, 5 Q, 23; 248/95

[56] References Cited

U.S. PATENT DOCUMENTS

| 2,595,934 | 5/1952 | Ginsburg | 128/283 |
| 3,897,785 | 8/1975 | Barto, Jr. | 128/295 |
| 3,919,615 | 11/1975 | Niecke | 224/5 H |

FOREIGN PATENT DOCUMENTS

| 620,541 | 5/1961 | Italy | 128/283 |

Primary Examiner—Robert W. Michell
Assistant Examiner—Henry S. Layton
Attorney, Agent, or Firm—Ralph F. Staubly

[57] ABSTRACT

A carrier and skin-protecting cover for disposable urine bags comprises one or more pouches and a waist-encircling support belt all made of permanent-press cotton fabric. The pouches are detachably fastened to the belt, and the belt is made adjustable by the use of "VELCRO" fasteners. The pouches desirably have iron-on patches for safety-pinning or otherwise fastening tubes in place, and have paired snaps for attaching the bags. The carrier requires no leg bands and has no skin-facing seams.

5 Claims, 4 Drawing Figures

CARRIER AND SKIN-PROTECTING COVER FOR URINE BAGS

This application is a continuation of identically entitled Ser. No. 685,983 filed May 13, 1976 now abandoned.

BACKGROUND AND OBJECTS OF THE INVENTION

While a few belt-supported bag holders are found in the prior art (e.g. Barto U.S. Pat. No. 3,897,785), for the most part urine bags have been usually placed directly against a patient's body and held there by adhesive material or tape, or by rubber straps.

It is accordingly the principal object of the present invention to provide a skin-protecting carrier for urine bags that is highly effective, comfortable to wear, easy to adjust, and inexpensive in acquisition and upkeep. Other objects and advantages will appear as the following detailed description proceeds.

With reference now to the drawings, the numeral 11 generally designates a preferred embodiment of the skin-protecting bag carrier. The carrier 11 comprises a belt 13 and one or more detachable pouches 15. Both parts are made of permanent-press cloth, preferably all or mostly cotton and constructed so that no seams face the body of a wearer.

Figure 2:
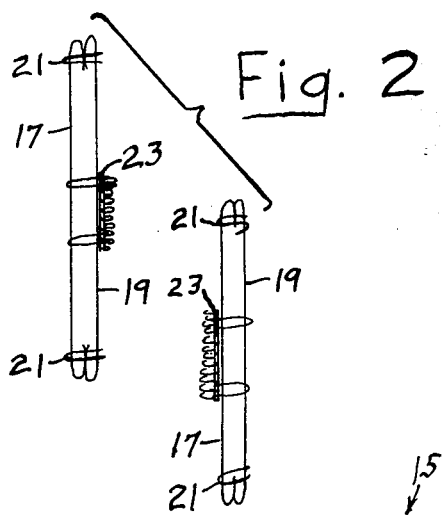
FIG. 2 is an enlarged fragmentary elevational view in section on the line 2—2 of FIG. 1.

The belt 13 consists of an outer strip 17 and in inner strip 19, the edges of which are inturned as shown in FIG. 2 and stitched together at 21. The belt end portions have stitched to their overlapping reaches, long strips 23 of "VELCRO" half pairs for quick, easy and secure length-adjustable connection.

The outer belt strip 17 also has stitched thereto spaced "VELCRO" strips 25 for similarly detachably gripping mating strips 27 stitched to the upper back surfaces of the pouches 15, a second pouch (shown in phantom in FIG. 1) being used, for example, when bilateral ostomies are encountered or when a spare bag is worn.

Figure 4:
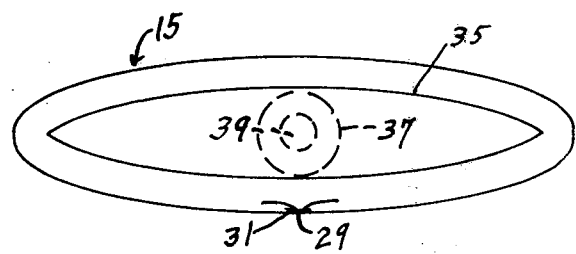
FIG. 4 is an enlarged plan view in section on the line 4—4 of FIG. 1.

Each pouch 15 is formed of a single cloth panel folded to have a front medial seam 29 stitched at 31 (FIG. 4). Each pouch 15 is also provided with a hemmed-edge opening 35 providing access to the top of the disposable urine bag 35 for easy connection and disconnection of conventional drainage tubes or catheters (not shown). The bottom of each pouch 15 is stitched shut except for a small central opening 37 through which the drainage nipple 39 extends. The conventional press-on or snap-on sealing cap for the nipple 39 is not shown.

Figure 1:
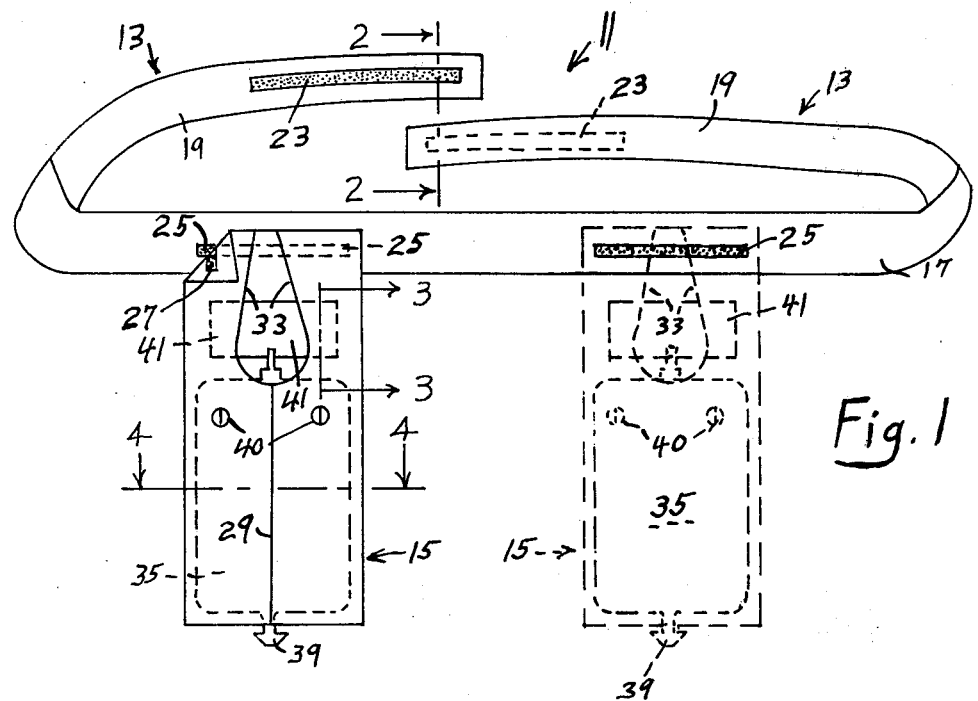
FIG. 1 is a front elevational view of a preferred embodiment of the invention.
Figure 3:
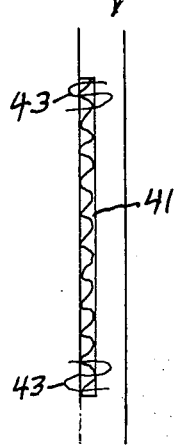
FIG. 3 is an enlarged fragmentary elevational view in section on the lined 3—3 of FIG. 1.

The front and rear panels of each puch 15 are provided with mating pairs of snap fasteners 40 positioned to engage through sealed holes in the removable urine bags, in known manner, to hold the bags positioned as shown in FIG. 1. The rear panel of each pouch 15 has a reinforcing patch 41 of heavy iron-on cloth positioned above the top of the bag 35 for safety-pinning, taping, or otherwise fastening the drainage tube (bit shown) in place. The patch 41 is also desirably marginally stitched at 43 (FIG. 3) to the rear panel of the pouch 15.

If it should be desired to shorten the pouches 15, their upper portions can be wrapped around the belt 13.

By eliminating the usual tight leg bands, by supporting the weight of the bag from a belt, and by making possible the positioning of the bag at various locations around, and out of irritating contact with, the body, the disclosed carrier contributes greatly to the comfort of the wearer.

Having thus described my invention, I claim:

1. A skin-protecting carrier for disposable urine bags of known construction and each having an input and an output drainage nipple, comprising: a body-encircling and usually-skin-contacting belt of soft relatively non-skin-irritating material, at least one bag-holding pouch of soft relatively non-skin-irritating material depending in usually-skin-contacting position from said belt and having a small opening in its bottom for extension therethrough of the drainage nipple of said bag, said pouch having an opening in the upper portion of its front panel to facilitate attachment and detachment of tubes to and from the input nipple of said bag, a reinforcing tubeanchoring patch fixed to the rear panel of said pouch opposite said opening, and pairs of mating snap-fasteners fixed to the front and rear panels of said pouch and positioned to bag-positioningly interengage through sealed openings in the upper corners of said bag of known construction.

2. Structure according to claim 1, said belt easily and quickly length-adjustable by having strips of VELCRO type fasteners thereon.

3. Structure according of claim 1, said pouch being detachably attached to said belt by VELCRO-type fasteners.

4. Structure according to claim 1, said belt and pouch having no body-facing seams.

5. Structure according to claim 1, said soft material being permanent-press cloth of high cotton-content.

* * * * *